United States Patent
Hekmatshoartabari et al.

(10) Patent No.: US 9,746,442 B2
(45) Date of Patent: Aug. 29, 2017

(54) SWITCHED-CAPACITOR BIOSENSOR DEVICE

(71) Applicant: International Business Machines Corporation, Armonk, NY (US)

(72) Inventors: Bahman Hekmatshoartabari, White Plains, NY (US); Ali Khakifirooz, Mountain View, CA (US); Ghavam G. Shahidi, Pound Ridge, NY (US); Davood Shahrjerdi, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 665 days.

(21) Appl. No.: 14/229,967

(22) Filed: Mar. 30, 2014

(65) Prior Publication Data
US 2015/0276653 A1  Oct. 1, 2015

(51) Int. Cl.
*G01N 27/403* (2006.01)
*G01N 27/414* (2006.01)

(52) U.S. Cl.
CPC .................. *G01N 27/4145* (2013.01)

(58) Field of Classification Search
CPC ........... G01N 27/414–27/417; G01N 27/4167; G01N 27/4145; G01N 27/4148; G01N 27/4166; G01N 27/301; G01N 27/302; G01N 27/333
See application file for complete search history.

(56) References Cited

U.S. PATENT DOCUMENTS

| | | | |
|---|---|---|---|
| 5,726,579 A | 3/1998 | Masuda | |
| 6,480,730 B2 | 11/2002 | Darrow | |
| 6,654,470 B1 | 11/2003 | Dilger | |
| 8,145,434 B2 | 3/2012 | Schakar | |
| 8,159,347 B2 | 4/2012 | Potyrailo | |
| 8,241,939 B2 | 8/2012 | Park | |
| 2005/0156584 A1 | 7/2005 | Feng | |
| 2007/0155037 A1 | 7/2007 | Chou | |
| 2010/0273672 A1* | 10/2010 | Demoustier-Champagne | G01N 33/54353 506/9 |
| 2011/0162979 A1 | 7/2011 | Shachar | |
| 2011/0166033 A1 | 7/2011 | Shachar | |
| 2011/0287977 A1 | 11/2011 | Cai | |
| 2012/0045368 A1 | 2/2012 | Hinz | |
| 2012/0187465 A1 | 7/2012 | Cheng | |
| 2013/0302932 A1* | 11/2013 | Bustillo | G01N 27/4145 438/49 |

FOREIGN PATENT DOCUMENTS

CN   202421115   9/2012

* cited by examiner

*Primary Examiner* — Gurpreet Kaur
(74) *Attorney, Agent, or Firm* — Louis J. Percello; Otterstedt, Ellenbogen & Kammer, LLP

(57) ABSTRACT

A sensing apparatus includes a device containing microwells and a switched capacitor circuit in which at least one of the sensing/storage capacitors is a capacitor that extends perpendicularly with respect to a semiconductor device layer containing field effect transistors. Capacitor structures extend into microwells or within a doped layer on a handle substrate. Ion generation within the microwells is sensed using the circuit.

15 Claims, 2 Drawing Sheets

SWITCHED-CAPACITOR BIOSENSOR DEVICE

FIELD

The present disclosure relates to the physical sciences and, more particularly, to capacitance sensors and their operation and fabrication.

BACKGROUND

Sensors have been developed for sensing or measuring various types of physical and chemical parameters. Differential capacitance detectors are among the technologies that have been developed.

Ion sensitive field effect transistor (ISFET) based sensors are commonly employed for sensing biochemical reactions. Changes in conductance within a test solution can be detected from changes in transistor conductance. For example, an ISFET sensor may be employed to detect the release of hydrogen as the byproduct of DNA base pairing. ISFET technology however presents various challenges, one of which is flicker (1/f) noise that is the dominant noise source in field-effect transistors. As the transistor dimensions are shrunk to improve the array density, the flicker noise intensity increases, hence limiting the resulting signal-to-noise ratio and scaling up the array density.

SUMMARY

Principles of the present disclosure provide an apparatus including an electrically insulating layer, a crystalline semiconductor layer adjoining a first side of the electrically insulating layer, and one or more switched capacitor circuits. Each switched capacitor circuit includes metal oxide semiconductor field effect transistors on the semiconductor layer, each of the transistors including source and drain regions. A plurality of capacitor structures extend perpendicularly with respect to the semiconductor layer, each of the capacitor structures being electrically connected to a pair of the transistors. The apparatus further includes a plurality of microwells. The capacitor structures and microwells are configured such that the one or more switched capacitor circuits are responsive to changes in ion concentration within one or more of the microwells.

A method provided in accordance with the principles described herein includes obtaining an apparatus including an electrically insulating layer, a crystalline semiconductor layer adjoining a first side of the electrically insulating layer, one or more a switched capacitor circuits, each switched capacitor circuit including a pair of metal oxide semiconductor field effect transistors on the semiconductor layer, each of the transistors including source and drain regions, a capacitor structure extending perpendicularly with respect to the semiconductor layer, and an electrical connection between the capacitor structure and the pair of the transistors, and a plurality of microwells. One or more fluids are introduced into the microwells. The method further includes detecting a change in ion concentration in the one or more fluids within the microwells using the switched capacitor circuit.

A further method includes obtaining a semiconductor on insulator substrate including a handle substrate, a crystalline semiconductor layer, and an electrically insulating layer between and directly contacting the handle substrate and crystalline semiconductor layer. A plurality of switched capacitor circuits is formed. This step includes forming a plurality of metal oxide semiconductor field effect transistors on the semiconductor layer, each of the transistors including source and drain regions, and forming a plurality of capacitor structures extending perpendicularly with respect to the semiconductor layer and electrically connected to a pair of the transistors. The method further includes forming a plurality of microwells, the capacitor structures and microwells being configured such that the switched capacitor circuits are responsive to changes in ion concentration within the microwells.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

Sensing devices as disclosed herein can provide substantial beneficial technical effects. For example, one or more embodiments may provide one or more of the following advantages:

Reduced noise sensitivity;
Allows upscaling of microwell array size;
Enhancing signal intensity due to increased sensor surface area using vertical wires.

These and other features and advantages will become apparent from the following detailed description of illustrative embodiments thereof, which is to be read in connection with the accompanying drawings.

DETAILED DESCRIPTION

A switched capacitor circuit incorporating a charge sensing device is disclosed in which at least one of the sensing/storage capacitors is a rod-shaped capacitor. High density arrays of rod-shaped capacitors facilitate sensing of conductivity changes caused by chemical reactions within test solutions in one or more embodiments.

Figure 1:
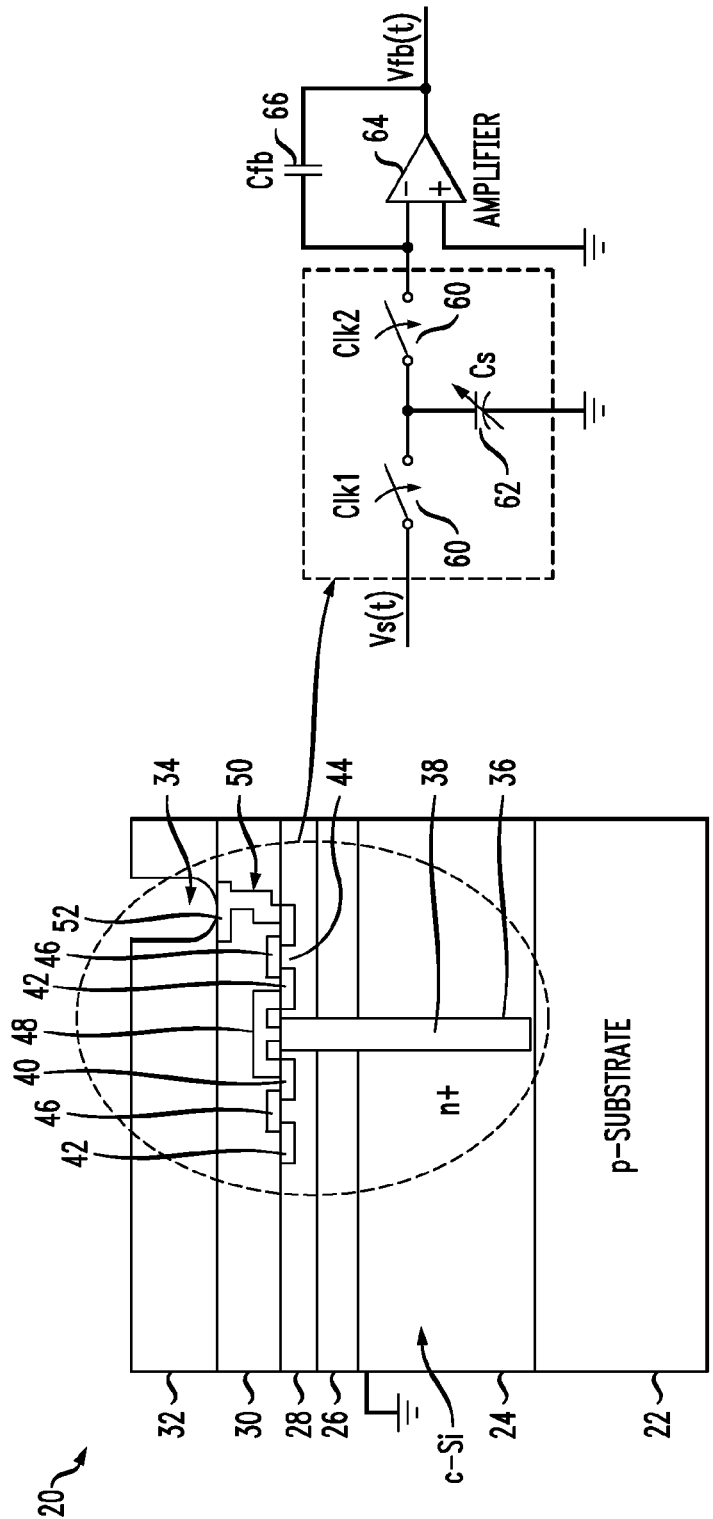
FIG. 1 is a schematic illustration of an exemplary charge sensing device.

An exemplary device 20 that can be employed in biosensing applications is shown in FIG. 1. Elements of the device are incorporated within a switched capacitor circuit such as a parasitic sensitive integrator. Switched capacitor circuits are characterized by moving charges into and out from capacitors when switches associated therewith are opened and closed (shorted). Switched capacitor circuits having various configurations are known in the art. The exemplary device 20 includes a substrate layer 22. The substrate layer comprises a lightly doped semiconductor material such as silicon that is p-type in the exemplary embodiment. The substrate layer 22 can be several hundred microns or more in thickness and can function as a handle as well as facilitate subsequent CMOS processing. A doped, n-type crystalline silicon layer 24 adjoins the substrate layer 22. The silicon layer can either be mono-crystalline or polycrystalline. This layer 24 has a thickness of 1-3 μm in one or more embodiments and can be formed either by ion implantation after fabrication of a semiconductor-on-insulator substrate that includes the substrate layer 22 or by epitaxial growth during fabrication of the substrate. The substrate layer is designated as p– and the crystalline silicon layer is designated as n+ in the drawing. Terms such as p– and n+ refer to doping types and relative doping concentrations, exemplary doping levels being identified below. In p-type semiconductors, holes are the majority carriers whereas electrons are the majority carriers in n-type semiconductors. For example, the n+ semiconductor layer 24 has a donor concentration exceeding $1 \times 10^{18}$ cm$^{-3}$ in one or more embodiments. The substrate layer has an acceptor concentration of $1 \times 10^{15}$ cm$^{-3}$ in one or more embodiments.

An electrically insulating layer 26 such as a buried oxide (BOX) layer adjoins the doped crystalline semiconductor layer 24. Silicon dioxide is among the materials that may be employed to form the electrically insulating layer. A device layer 28 adjoins the electrically insulating layer. Depending on the electronic circuitry to be formed, the thickness of the crystalline semiconductor layer (SOI layer) used to fabricate the device layer 28 can be in the range of three nanometers (3 nm) to two microns (2 μm). Various methods of fabricating semiconductor-on-insulator (SOI) substrates as employed in one or more embodiments are known, one of which is Separation-by-Implanted Oxygen (SIMOX), wherein oxygen is ion implanted into a single crystal silicon substrate to form a BOX film. Another method of forming an SOI substrate is through SMART CUT® method and wafer bonding, wherein two semiconductor substrates with silicon oxide surface layers are bonded together at the silicon oxide surfaces to form a BOX layer between the two semiconductor substrates. Doping of SOI substrates can be adjusted during fabrication. For example, the top 1-3 μm of a lightly doped p– silicon handle substrate can be implanted with phosphorus to form the n-type layer 24. SOI substrates are also commercially available.

A second electrically insulating layer 30 adjoins the device layer 28. The second electrically insulating layer may comprise silicon dioxide or relatively low-k materials. (Low-k materials have dielectric constants lower than that of silicon dioxide.) This layer may be formed during conventional back-end-of-line (BEOL) processing. A third electrically insulating layer 32, which is a silicon dioxide layer in some embodiments, adjoins the second electrically insulating layer. Microwells 34 are formed in the third electrically insulating layer. Wet etch and reactive ion etch (RIE) are processes that may be employed to form an array of microwells in the third (top) insulating layer.

A trench is provided within the doped, n-type silicon layer 24. The sidewall of the trench includes a dielectric layer 36 comprised of high-k material(s) and possibly silicon dioxide. Alternatively, hafnium oxide or other high-k materials may comprise the dielectric layer 36. An electrically conductive material fills the trench, forming a rod-like core 38 that extends perpendicularly to the device layer. In one or more embodiments, the electrically conductive material is n+ polysilicon. As discussed further below, the adjoining n+ regions 38, 24 and dielectric layer 36 therebetween together function as a variable capacitor 62 within a switched capacitor circuit. In one or more embodiments, the trenches employed to form elements of the capacitors have depths between 200 nm-5 μm and diameters of 100 nm-1 μm. While only one trench is shown, additional trenches, microwells and associated circuitry are further included in the device 20.

The spacing between trenches, which corresponds to capacitor spacing, ranges from 100 nm-500 nm in one or more embodiments. In one or more embodiments, the trenches are formed through a deep reactive ion etch process. Subsequently, an atomic layer deposition (ALD) or chemical vapor deposition (CVD) process is employed to coat the trench sidewalls with a high-k dielectric material such as hafnium oxide. An additional thermal oxidation process may be performed to form silicon dioxide on the trench sidewalls prior to the deposition of the high-k material. Highly doped polysilicon is then deposited using a CVD process to fill the trenches.

The device layer 28 contains doped regions that form the source/drain regions of CMOS field effect transistors (MOSFETs). Referring to FIG. 1, source regions 40 and drain regions 42 are shown. Channel regions 44 are associated with each transistor. Gate structures 46 are formed on the device layer above the channel regions 44. The gate structures include gate electrodes and gate dielectric layers between the gate electrodes and channel regions. Metal layers are formed are formed within the second dielectric layer 30. The source region 40 of one transistor is thereby electrically connected to the drain region 42 of an adjoining transistor. The capacitor is connected in series with the two adjoining transistors by an electrical connection with the n+ polysilicon element 38 formed within the trench. An exemplary metal structure 48 connecting the transistors and capacitor is shown schematically in FIG. 1. The drain region 42 of one of the transistors (corresponding to switch FET1) is electrically connected to a further metal structure 50 that includes a metal contact 52 adjoining the bottom of the microwell 34. A high-k dielectric layer (not shown) is provided between the contact and the microwell in some embodiments so that sample solutions contained within the microwell contact the high-k dielectric layer rather than the metal contact 52. Conventional CMOS and back-end-of-line processing techniques familiar to those of skill in the art can be employed for forming the field effect transistors and associated metal layers.

As further shown in FIG. 1, the field effect transistors and associated capacitor are incorporated as part of a switched capacitor circuit. The field effect transistors (40-46) function as a pair of switches 60 that can, in alternating sequence, be open or closed (shorted). The capacitor is functional as a variable capacitor 62 between the switches. If incorporated as part of a parasitic sensitive integrator circuit, one of the field effect transistors is electrically connected to an operational amplifier 64. A variable voltage Vs(t) input to the circuit results from chemical reaction(s) within the microwell 34 that affect an applied voltage. If the first switch 60 is short while the second switch is open, the variable capacitor is charged. If the first switch is open and the second switch is closed, the charge of the variable capacitor 64 is shared with a feedback capacitor 66 (Cm). A feedback voltage Vfb(t) outputted by the circuit is indicative of reactions within the microwell that are detected by the circuit. The n+ layer 24 may be employed for resetting the array of capacitors formed therein through the application of a high voltage. It will be appreciated that switched capacitor circuits configured differently from those shown and described with respect to the exemplary embodiments may be employed in one or more alternative embodiments. A charge sensing amplifier circuit including an op-amp and a feedback capacitor (not shown) is employed in one alternative embodiment.

Figure 2:
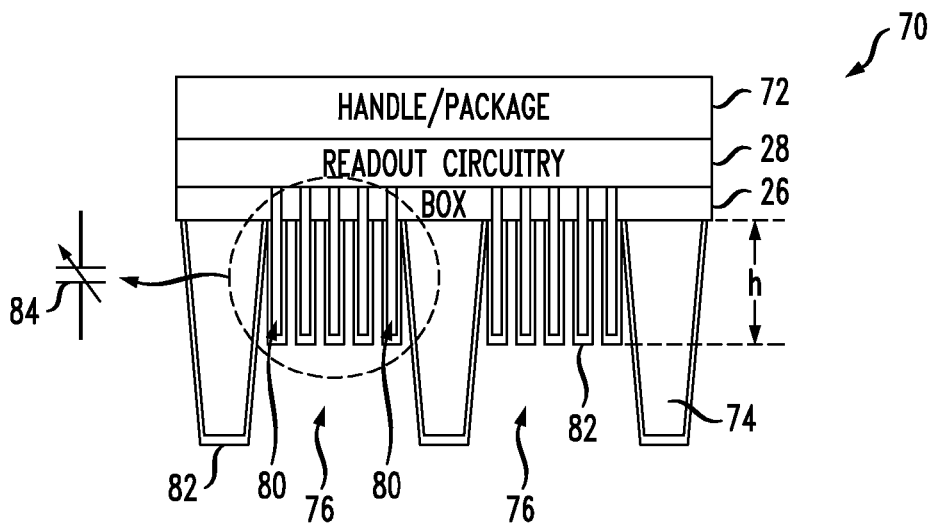
FIG. 2 is a schematic illustration of an alternative embodiment of a charge sensing device.

A second exemplary sensing device 70 is shown schematically in FIG. 2. The device includes a crystalline silicon device layer 28 on an electrically insulating layer 26. The device layer contains CMOS field effect transistor elements similar to those described with respect to FIG. 1. A handle/package layer 72 is formed on the device layer 28. The handle/package layer 72 comprises multiple layers in one or more embodiments. Metal layers and gate structures may be incorporated in a dielectric layer incorporated within the handle/package layer. The device further includes a crystalline silicon handle layer 74 adjoining the surface of the electrically insulating layer opposite from the surface that adjoins the device layer 28. Microwells 76 are formed in the silicon handle layer 74. A plurality of rod-like columns 78 extend within each microwell. Each column includes an n+ polysilicon core 80 and a dielectric layer 82 of high-k material adjoining the core. The cores 80 and dielectric layer 82 form capacitor structures that extend perpendicularly to the device layer 28. The dielectric layer 82 is an oxide layer such as hafnium oxide in some embodiments and a nitride layer ($Si_3N_4$) in other embodiments. The dielectric layer 82 electrically isolates the polysilicon cores 80 from solution introduced into the microwells 76. The dielectric layer 82 is also formed over the silicon handle layer 74 and also isolates the side walls of the microwells from any materials contained within the microwells. The contents of the microwells, when used for testing, typically contain ions in solution and are accordingly conductive. Ions such as H+ in solution are good charge carriers. The n-type cores 80 and the solution can accordingly form "plates" of capacitors 84 capable of storing charges following application of a DC bias to the solution. Each capacitor 84 is electrically connected between a pair of CMOS field effect transistors formed using the crystalline silicon layer 28 as part of a switched capacitor circuit. It will be appreciated that the numbers of capacitor structures formed within each well may be greater or less than that shown in the schematic illustration.

The device can be fabricated from an SOI substrate that includes a crystalline silicon layer used to form the device layer 28, the electrically insulating layer 26, and a silicon base layer that forms a handle substrate layer 74. FETs are formed using the crystalline silicon layer. Conventional CMOS processing can be employed to form the readout circuitry. Once CMOS and BEOL processing is completed, the handle/package 72 is bonded to the processed SOI substrate. The silicon handle layer 74 is then thinned to a thickness corresponding to the desired depths of the microwells 76 (e.g. 3-20 μm). Mechanical grinding and controlled spalling are among the processes that may be employed for thinning the silicon base layer. The thinned silicon layer is then patterned and subjected to an anisotropic aqueous KOH etch or other anisotropic etch to form the microwells 76. Etching of crystalline silicon is highly anisotropic, the (100) plane etching quickly while the (111) plane has the slowest etch rate. Using (100) oriented silicon, the surfaces of the trenches formed within the silicon converge inwardly to form microwells having relatively large openings. The sizes of the openings within the etch mask (not shown) and the thickness of the silicon layer are chosen such that the silicon layer is etched down to the electrically insulating layer 26, which acts as an etch stop. Sufficient areas of the electrically insulating layer are exposed to allow the formation of one or more elements that function as components of capacitors when the device is completed. The electrically insulating layer is patterned and etched to form passages extending to the device layer 28. Hydrofluoric acid is a wet etchant that can be used in one or more embodiments for forming the passages in an electrically insulating layer formed from silicon dioxide. A polysilicon layer is deposited within the microwells and the passages within the electrically insulating layer 26. Doping of the polysilicon layer to form an electrically conductive n+ layer may be effected during deposition. The deposition of polysilicon is familiar to those of skill in the art. Processes such as low pressure chemical vapor deposition (LPCVD) may be employed to deposit polysilicon. Phosphorus is an exemplary doping impurity for forming n-type layers. The polysilicon layer is patterned and etched to form the core portions 80 of the columns, which are electrically connected to the device layer 28. The oxide or nitride dielectric layer 82 is then deposited on the structure. Techniques as described above with respect to FIG. 1 can be employed for forming the dielectric layer 82. The columns formed by the core portions 80 and dielectric layer 82 have heights h that are smaller than the depths of the microwells 76. In some embodiments, the column heights h are between 200 nm and 5 μm, column diameters between 100 nm-1 μm and the spacing between columns ranges from 100-500 nm. As discussed above, capacitors 84 electrically connected with the readout circuitry in the device layer 28 are formed by the core portions 80, dielectric layer 82 and test solution contained by the microwells when the device 70 is in use.

Figure 3:
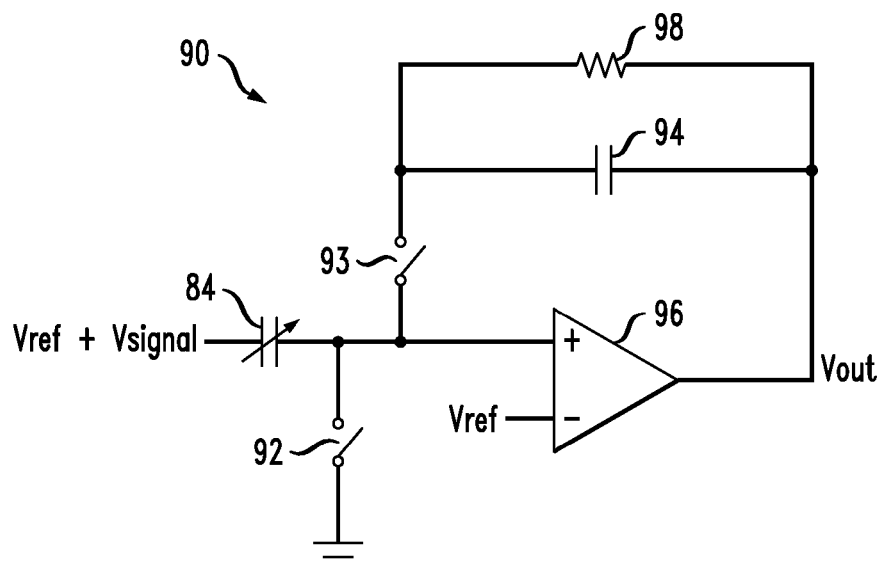
FIG. 3 is a circuit diagram showing an exemplary switched capacitor circuit that incorporates elements of the charge sensing device shown in FIG. 2.

FIG. 3 shows an exemplary switched capacitor circuit 90 for charge sensing using a device 70 as shown in FIG. 2. The variable capacitor 84 formed by the test solution and columns in the microwell is connected between a pair of CMOS field effect transistors contained in the device layer 28. The columns formed by the core portions 80 and dielectric layer 82 collectively form an element of one variable capacitor. The transistors form switches 92, one of which is between the variable capacitor 84 and a switch capacitor 94. The second switch can be shorted to ground. In this exemplary embodiment, the two inputs to an amplifier 96 include a reference voltage $V_{ref}$ and $V_{ref}+V_{signal}$, respectively, the latter reflecting conductive changes in the test solution within the microwells. The circuit further includes a resistor 98 connected to the switch capacitor 94. When the switch 92 is short, the variable capacitor 84 is charged by the signal voltage (if present). Subsequently, the switch 92 is opened, the switch 93 is short, and the capacitor 94 is charged.

Given the discussion thus far and with reference to the exemplary embodiments discussed above and the drawings, it will be appreciated that, in general terms, an exemplary apparatus includes an electrically insulating layer 26 and a crystalline semiconductor layer adjoining a first side of the electrically insulating layer. The apparatus includes one or more switched capacitor circuits, each switched capacitor circuit including metal oxide semiconductor field effect transistors on the semiconductor layer, each of the transistors including source and drain regions 40, 42. A plurality of capacitor structures (80, 82 in the exemplary device 70; 38, 36 in the exemplary device 20) extend perpendicularly with respect to the semiconductor layer, each of the capacitor structures being electrically connected to a pair of the transistors. The apparatus further includes a plurality of microwells (76 in the device 70, 34 in the device 20) the capacitor structures and microwells being configured such that the one or more switched capacitor circuits are responsive to changes in ion concentration within one or more of the microwells. Exemplary switched capacitor circuits are shown in FIGS. 1 and 3. In some embodiments, the microwells 76 extend within the handle substrate and the capacitor structures extend within the microwells. Each microwell 76 contains a plurality of capacitor structures in one or more embodiments. The handle substrate can comprise crystalline silicon. Each microwell 76 has an opening and side walls that taper inwardly from the opening in the direction of the electrically insulating layer 26 in some embodiments. The capacitor structures in exemplary embodiments each include an electrically conductive core 38 or 80 and a dielectric coating 36 or 82 over the core. Each microwell 76 has a depth greater than the heights of the capacitor structures within the microwells. Cores comprising n-type polysilicon are employed in one or more embodiments. The apparatus further includes a sample solution containing ions within the microwells in some embodiments, the sample solution and the electrically conductive core 80 of the capacitor structure comprising opposing conductive elements of a capacitor separated by the dielectric coating 82. In some embodiments as exemplified by the device 20 shown in FIG. 1, the apparatus further includes a doped semiconductor layer 24 adjoining a second side of the electrically insulating layer 26, each of the capacitor structures including a doped, electrically conductive core 38 and a dielectric coating 36 over the core, the capacitor structures extending into the doped semiconductor layer 24 such that the dielectric coating 36 directly contacts the doped semiconductor layer 24. An electrical contact 52 adjoins each microwell 34, each electrical contact being electrically connected to the source region 40 of the transistors. In some embodiments thereof, each capacitor structure has a diameter between 100 nm-1 µm. Capacitor spacing may be 100-500 nm in one or more embodiments.

An exemplary method includes obtaining an apparatus including an electrically insulating layer 26, a crystalline semiconductor layer adjoining a first side of the electrically insulating layer, one or more a switched capacitor circuits, each switched capacitor circuit including a pair of metal oxide semiconductor field effect transistors on the semiconductor layer, each of the transistors including source and drain regions 40, 42, a capacitor structure extending perpendicularly with respect to the semiconductor layer, and an electrical connection between the capacitor structure and the pair of the transistors. The apparatus further includes a plurality of microwells 34, 76 such as shown in FIGS. 1 and 2, respectively. One or more fluids are introduced into the microwells. The method further includes detecting a change in ion concentration in the one or more fluids within the microwells using the switched capacitor circuit. As discussed above, such detection is enabled by capacitor structures that directly contact the one or more fluids, such as described with respect to the device 70 shown in FIG. 2, or which are electrically connected to contacts that adjoin the microwells and are thereby sensitive to changes in the ionic content (e.g. H+ content) of the fluids. The switches electrically associated with the capacitor structures, which are MOSFETs formed using the crystalline semiconductor layer (SOI layer), are opened and closed in alternating sequence in using the switched capacitor circuit. The switching frequency will depend in part on the chemical reaction rate to ensure adequate time for charging the variable capacitor 84. In some embodiments of the method, the apparatus further includes a handle substrate 74 adjoining a second side of the electrically insulating layer 26, the microwells extending within the handle substrate, the capacitor structure of each switched capacitor circuit extending within one of the microwells 76, each capacitor structure including an electrically conductive core 80 and a dielectric coating 82 over the core, each microwell 76 having a depth greater than the heights of the capacitor structures. The one or more fluids contact the dielectric coatings 82 of each capacitor structure and a DC bias is applied to the one or more fluids within the microwells 76. Changes in the ionic concentration of the sample fluid(s) are sensed by the capacitors formed by the capacitor structures and adjoining fluid(s). In one or more embodiments, such as shown in FIG. 2, each microwell 76 contains a plurality of parallel capacitor structures so that the one or more fluids contact the plurality of parallel capacitor structures in each microwell. In alternative embodiments employed devices such as the device 20 shown in FIG. 1, the apparatus further includes a doped semiconductor layer adjoining a second side of the electrically insulating layer, the capacitor structure includes a doped, electrically conductive core and a dielectric coating over the core, the capacitor structure extends into the doped semiconductor layer such that the dielectric coating directly contacts the doped semiconductor layer, and an electrical contact adjoins each microwell. Each electrical contact 52 is electrically connected to the source region of one of the transistors. The method further includes causing the one or more fluids to adjoin the electrical contacts 52. In one or more embodiments, the test fluids include polymer particles or microbeads configured to enhance the chemical signal by the target molecules. Either device 20, 70 can be incorporated within a flow chamber (not shown) such that reagent flows across an array of microwells formed in the device. Change in the surface charge near the bottoms of the microwells is detected by the switched capacitor circuits. In one exemplary embodiment, a DNA sequencing process is characterized by a change in pH of the sample solution(s) within the microwells.

Fabrication methods are further provided, as discussed above. In some embodiments, microwells 76 are formed on the handle substrate and capacitor structures are formed within the microwells. In other embodiments, the microwells 34 are formed in an electrically insulating layer 32 above the device layer 28 and the capacitor structures are formed in a doped semiconductor layer 24 beneath the device layer 28. MOSFETs on the device layer 28 are electrically connected to the capacitor structures, forming parts of a switched capacitor circuit that can be used for sensing the production of ions within the microwells. Arrays of microwells and associated circuitry can be employed for bio-sensing applications such as DNA sequencing.

Those skilled in the art will appreciate that the exemplary structures discussed above can be distributed as complete systems or as parts of intermediate products or end products that benefit from having capacitive sensors therein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

The corresponding structures, materials, acts, and equivalents of all means or step plus function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the various embodiments with various modifications as are suited to the particular use contemplated.

What is claimed is:

1. An apparatus comprising:
an electrically insulating layer;
a crystalline semiconductor layer adjoining a first side of the electrically insulating layer;
a handle substrate adjoining a second side of the electrically insulating layer;
one or more switched capacitor circuits, each of the one or more switched capacitor circuits including metal oxide semiconductor field effect transistors on the crystalline semiconductor layer, each of the transistors including source and drain regions;
a plurality of capacitor structures extending perpendicularly with respect to the crystalline semiconductor layer, each of the plurality of capacitor structures being electrically connected to a pair of the transistors, and
a plurality of microwells extending within the handle substrate, the plurality of capacitor structures extending within the plurality of microwells, the plurality of capacitor structures and the plurality of microwells being configured such that the one or more switched capacitor circuits are responsive to changes in ion concentration within one or more of the plurality of microwells.

2. The apparatus of claim 1, wherein each of the plurality of microwells contains a plurality of rod-like columns, each of the plurality of rod-like columns including an electrically conductive core and a dielectric layer on the electrically conductive core; each of the plurality of capacitor structures being comprised of the plurality of rod-like columns contained, respectively, within each of the plurality of microwells.

3. The apparatus of claim 2, wherein, each of the plurality of microwells includes an opening and side walls that taper inwardly from the opening in the direction of the electrically insulating layer.

4. The apparatus of claim 2, wherein each of the plurality of microwells has a depth greater than the heights of the plurality of rod-like columns contained therein.

5. The apparatus of claim 4, wherein each electrically conductive core comprises n-type polysilicon.

6. The apparatus of claim 4, further including a sample solution containing ions within the plurality of microwells and adjoining the plurality of rod-like columns.

7. A method comprising:
obtaining an apparatus including:
an electrically insulating layer,
a crystalline semiconductor layer adjoining a first side of the electrically insulating layer,
a handle substrate adjoining a second side of the electrically insulating layer;
one or more switched capacitor circuits, each of the one or more switched capacitor circuits including metal oxide semiconductor field effect transistors on the crystalline semiconductor layer, each of the transistors including source and drain regions;
a plurality of capacitor structures extending perpendicularly with respect to the crystalline semiconductor layer, each of the plurality of capacitor structures being electrically connected to a pair of the transistors, and
a plurality of microwells extending within the handle substrate, the plurality of capacitor structures extending within the plurality of microwells, the plurality of capacitor structures and the plurality of microwells being configured such that the one or more switched capacitor circuits are responsive to changes in ion concentration within one or more of the plurality of microwells;
introducing one or more fluids into the plurality of microwells, and
detecting a change in ion concentration in the one or more fluids within the plurality of microwells using the one or more switched capacitor circuits.

8. The method of claim 7, wherein each of the plurality of capacitor structures includes an electrically conductive core and a dielectric coating over the core, each of the plurality of microwells having a depth greater than the heights of the plurality of capacitor structures, further including the steps of causing the one or more fluids to contact the dielectric coating of each of the plurality of capacitor structures and applying a DC bias to the one or more fluids within the plurality of microwells.

9. The method of claim 7, wherein each of the plurality of microwells contains a plurality of parallel rod-like columns, each of the plurality of parallel rod-like columns including an electrically conductive core and a dielectric layer on the electrically conductive core, each of the plurality of capacitor structures being comprised of the plurality of parallel rod-like columns contained, respectively, within each of the plurality of microwells; further including causing the one or more fluids to contact the plurality of parallel columns in the plurality of microwells.

10. The method of claim 7, wherein each electrically conductive core comprises n-type polysilicon.

11. An apparatus comprising:
an electrically insulating layer;
a crystalline semiconductor layer adjoining a first side of the electrically insulating layer;
a doped semiconductor layer adjoining a second side of the electrically insulating layer;
one or more switched capacitor circuits, each of the one or more switched capacitor circuits including metal oxide semiconductor field effect transistors on the crystalline semiconductor layer, each of the transistors including source and drain regions;
a plurality of capacitor structures extending perpendicularly with respect to the crystalline semiconductor layer, each of the plurality of capacitor structures including a doped, electrically conductive core and a dielectric coating over the core, each of the plurality of capacitor structures extending into the doped semiconductor layer such that the dielectric coating directly contacts the doped semiconductor layer, each of the plurality of capacitor structures being electrically connected to a pair of the transistors;
a plurality of microwells, the plurality of capacitor structures and the plurality of microwells being configured such that the one or more switched capacitor circuits are responsive to changes in ion concentration within one or more of the plurality of microwells, and
electrical contacts respectively adjoining each of the plurality of microwells, each of the electrical contacts being electrically connected to the source region of one of the transistors.

12. The apparatus of claim 11, further including an operational amplifier and a feedback capacitor, wherein the operational amplifier, the feedback capacitor, a pair of the transistors, and one of the plurality of capacitor structures are configured as a parasitic sensitive integrator circuit.

13. The apparatus of claim 11, wherein the doped semiconductor layer and the doped, electrically conductive core of each of the plurality of capacitor structures have n-type conductivity.

14. The apparatus of claim 11, further including a top electrically insulating layer above the first side of the electrically insulating layer and above the crystalline semiconductor layer, the plurality of microwells extending into the top electrically insulating layer.

15. The apparatus of claim 11, wherein each of the plurality of capacitor structures has a diameter between 100 nm-1 μm.

* * * * *